US012299780B2

(12) United States Patent
Peng et al.

(10) Patent No.: US 12,299,780 B2
(45) Date of Patent: May 13, 2025

(54) METHODS AND SYSTEMS FOR RECONSTRUCTING A POSITRON EMISSION TOMOGRAPHY IMAGE

(71) Applicant: CANON MEDICAL SYSTEMS CORPORATION, Otawara (JP)

(72) Inventors: Peng Peng, Vernon Hills, IL (US); Yi Qiang, Vernon Hills, IL (US); Wenyuan Qi, Vernon Hills, IL (US); Xiaoli Li, Vernon Hills, IL (US); Li Yang, Vernon Hills, IL (US)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 579 days.

(21) Appl. No.: 17/237,975

(22) Filed: Apr. 22, 2021

(65) Prior Publication Data
US 2022/0343566 A1  Oct. 27, 2022

(51) Int. Cl.
*G06T 7/00* (2017.01)
*A61B 6/03* (2006.01)
*G06T 11/00* (2006.01)

(52) U.S. Cl.
CPC .......... *G06T 11/006* (2013.01); *G06T 7/0012* (2013.01); *A61B 6/037* (2013.01);
(Continued)

(58) Field of Classification Search
CPC ..... A61B 6/037; A61B 6/5205; G06T 11/006; G06T 7/0012; G06T 2207/10081; G06T 2207/10104
See application file for complete search history.

(56) References Cited

U.S. PATENT DOCUMENTS 7,636,461 B2   12/2009 Spies et al.
8,600,139 B2   12/2013 Zhang et al.
(Continued)

FOREIGN PATENT DOCUMENTS

CN   102483852 B   8/2016

OTHER PUBLICATIONS

"Mathematics and Physics of Emerging Biomedical Imaging." 1996. Retrieved from https://www.ncbi.nlm.nih.gov/books/NBK232475/.
(Continued)

*Primary Examiner* — Amandeep Saini
*Assistant Examiner* — Mehrazul Islam
(74) *Attorney, Agent, or Firm* — Oblon, McClelland, Maier & Neustadt, L.L.P.

(57) ABSTRACT

An apparatus for reconstructing a positron emission tomography (PET) image, comprising processing circuitry configured to extract, from raw data obtained from a PET scanner, energy data and timing data associated with a plurality of annihilation events, the extracted energy data and the extracted timing data for each annihilation event corresponding to interactions between each of a pair of gamma rays generated by each annihilation event and one or more gamma ray detectors of the PET scanner, classify each annihilation event based on respective extracted energy data and respective extracted timing data, determine, for each annihilation event and based on a calculated timing resolution of the annihilation event, a width of a time-of-flight kernel, and reconstruct, by processing circuitry, the PET image based on the obtained raw data from the PET scanner and the determined width of the time-of-flight kernel associated with each annihilation event.

4 Claims, 12 Drawing Sheets

(52) U.S. Cl.
CPC ............... *G06T 2207/10081* (2013.01); *G06T 2207/10104* (2013.01)

(56) References Cited

U.S. PATENT DOCUMENTS

| | | | |
|---|---|---|---|
| 2007/0085013 A1* | 4/2007 | Watson | G01T 1/2985 |
| | | | 250/363.07 |
| 2010/0166274 A1 | 7/2010 | Busch et al. | |
| 2013/0026370 A1* | 1/2013 | Qian | G06T 11/005 |
| | | | 250/362 |
| 2015/0192685 A1* | 7/2015 | Griesmer | G01T 1/1647 |
| | | | 250/362 |
| 2019/0108904 A1* | 4/2019 | Zhou | G06T 5/002 |
| 2019/0287275 A1* | 9/2019 | Zhu | G06T 11/006 |
| 2019/0365341 A1* | 12/2019 | Chan | A61B 6/5258 |
| 2021/0093279 A1* | 4/2021 | Zhang | A61B 6/4233 |
| 2022/0155471 A1* | 5/2022 | Blevis | G01T 1/2964 |

OTHER PUBLICATIONS

Vandenberghe, S. et al., "Recent developments in time-of-flight PET" 2016. DOI 10.1186/s40658-016-0138-3.

Surti, S. "Update on Time-of-Flight PET Imaging" 2015. DOI: 10.2967/jnumed.114.14502.

Ote, K. et al., "M-01-079—Direct Annihilation Position Classification based on Deep Learning using Pair of Cherenkov Detectors: Monte Carlo Study (#1920)" 2019. Retrieved from https://www.eventclass.org/contxt_ieee2019/online-program/mobile-get-session-details.

\* cited by examiner

|  | Single-crystal events | Multi-crystal events |
|---|---|---|
| Percentage | 62.8 % | 37.2 % |
| Timing resolution | $\Delta t_1$ | $\Delta t_2, \Delta t_3$ |

FIG. 8

METHODS AND SYSTEMS FOR RECONSTRUCTING A POSITRON EMISSION TOMOGRAPHY IMAGE

BACKGROUND

Field of the Disclosure

The present disclosure relates to diagnostic imaging systems and methods. In particular, the present disclosure relates to positron emission tomography.

Description of the Related Art

Positron emission tomography (PET) imaging begins with the administration (e.g., through ingestion or inhalation) of a radiopharmaceutical agent to a patient. In time, the radiopharmaceutical agent concentrates at specific locations in the human body, thereby exploiting physical and biomolecular properties of the radiopharmaceutical agent to accumulate at regions of interest. The actual spatial distribution, intensity of the point or region of accumulation, and kinetics of the PET imaging process, from administration to capture to elimination, are all elements that may have clinical significance.

During the PET imaging process, the positron emitter attached to the pharmaceutical agent will emit positrons according to the physical properties of the isotope. Emitted positrons collide with an electron of the imaging object, or patient, resulting in an annihilation of the positron and electron and generation of two gamma rays at 511 keV in opposite directions. PET scanners, which include several PET detector rings for detecting the generated gamma rays, typically include a cylindrical bore-type housing supporting the several PET detector rings. Each of the two generated gamma rays interacts with PET detectors of the several PET detector rings and a signal is registered.

Traditionally, in order to estimate a location at which the two gamma rays were generated between the impacted PET detectors, PET system image reconstruction techniques relied on a uniform probability that the location of the 'annihilation event' occurred at any given point between the two impacted PET detectors. With higher timing precision, however, PET imaging systems are able to measure the time-of-flight (TOF) difference between the two generated, coincident gamma rays, or annihilation photons. Thus, image reconstruction techniques can rely on an improved spatial estimation of where the annihilation event occurred through integration of a TOF kernel. Often, this TOF kernel assumes that the timing resolution of the PET system is uniform over all annihilation events, allowing an average time resolution to be used in all cases.

Under ideal conditions, wherein each annihilation event results in two gamma rays that fully deposit their energy within a respective one PET detector, using an average TOF kernel is acceptable. However, over 30% of annihilation events do not result in 'single crystal' events. Thus, traditional techniques do not allow for optimal image reconstruction under non-ideal circumstances, and a new approach is needed.

The foregoing "Background" description is for the purpose of generally presenting the context of the disclosure. Work of the inventors, to the extent it is described in this background section, as well as aspects of the description which may not otherwise qualify as prior art at the time of filing, are neither expressly or impliedly admitted as prior art against the present invention.

SUMMARY

The present disclosure relates to a positron emission tomography scanner and methods for image reconstruction that accommodate varying timing resolutions.

According to an embodiment, the present disclosure further relates to an apparatus for reconstructing a positron emission tomography image, comprising processing circuitry configured to extract, from raw data obtained from a positron emission tomography scanner, energy data and timing data associated with a plurality of annihilation events, the extracted energy data and the extracted timing data for each annihilation event corresponding to interactions between each of a pair of gamma rays generated by each annihilation event and one or more gamma ray detectors of the positron emission tomography scanner, classify each annihilation event based on respective extracted energy data and respective extracted timing data, calculate a timing resolution for each annihilation event based on the classification, determine, for each annihilation event and based on the calculated timing resolution of the annihilation event, a width of a time-of-flight kernel, and reconstruct, by processing circuitry, the positron emission tomography image based on the obtained raw data from the positron emission tomography scanner and the determined width of the time-of-flight kernel associated with each annihilation event.

According to an embodiment, the present disclosure further relates to a method for reconstructing a positron emission tomography image, comprising extracting, by processing circuitry and from raw data obtained from a positron emission tomography scanner, energy data and timing data associated with a plurality of annihilation events, the extracted energy data and the extracted timing data for each annihilation event corresponding to interactions between each of a pair of gamma rays generated by each annihilation event and one or more gamma ray detectors of the positron emission tomography scanner, classifying, by the processing circuitry, each annihilation event based on respective extracted energy data and respective extracted timing data, calculating, by the processing circuitry, a timing resolution for each annihilation event based on the classification, determining, by the processing circuitry and for each annihilation event, a width of a time-of-flight kernel, and reconstructing, by the processing circuitry, the positron emission tomography image based on the obtained raw data from the positron emission tomography scanner and the determined width of the time-of-flight kernel associated with each annihilation event.

According to an embodiment, the present disclosure further relates to a non-transitory computer-readable storage medium storing computer-readable instructions that, when executed by a computer, cause the computer to perform a method for reconstructing a positron emission tomography image, comprising extracting, from raw data obtained from a positron emission tomography scanner, energy data and timing data associated with a plurality of annihilation events, the extracted energy data and the extracted timing data for each annihilation event corresponding to interactions between each of a pair of gamma rays generated by each annihilation event and one or more gamma ray detectors of the positron emission tomography scanner, classifying each annihilation event based on respective extracted energy data and respective extracted timing data, calculating a timing resolution for each annihilation event based on the classification, determining, for each annihilation event and based on the calculated timing resolution of the annihilation event, a width of a time-of-flight kernel, and reconstructing the positron emission tomography image based on the obtained raw data from the positron emission tomography scanner and the determined width of the time-of-flight kernel associated with each annihilation event.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 8 is a tabular representation of, for all gamma rays, a percentage of gamma rays involved in single-crystal events or multi-crystal events, according to an exemplary embodiment of the present disclosure;

DETAILED DESCRIPTION

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). Reference throughout this document to "one embodiment", "certain embodiments", "an embodiment", "an implementation", "an example" or similar terms means that a particular feature, structure, or characteristic described in connection with the embodiment is included in at least one embodiment of the present disclosure. Thus, the appearances of such phrases or in various places throughout this specification are not necessarily all referring to the same embodiment. Furthermore, the particular features, structures, or characteristics may be combined in any suitable manner in one or more embodiments without limitation.

The terms "detector crystal" and "crystal" are used interchangeably and are meant to describe a similar component of the imaging system, as will be described with reference to FIG. 9 and FIG. 10.

Positron emission tomography (PET) is based on the principle of opposed 511 keV photons originating from an annihilation of an emitted positron with a nearby electron. In conventional PET, coincidence electronics are used to determine along which line of response (LOR) an annihilation has occurred. As introduced earlier, conventional approaches, in an effort to localize the annihilation, rely on an equal likelihood that the annihilation occurred at any given point along the LOR. Time-of-flight (TOF) PET goes one step further, determining the likely position of annihilation along the LOR by measuring a difference in arrival times of each photon with a respective PET detector(s).

Figure 1C:
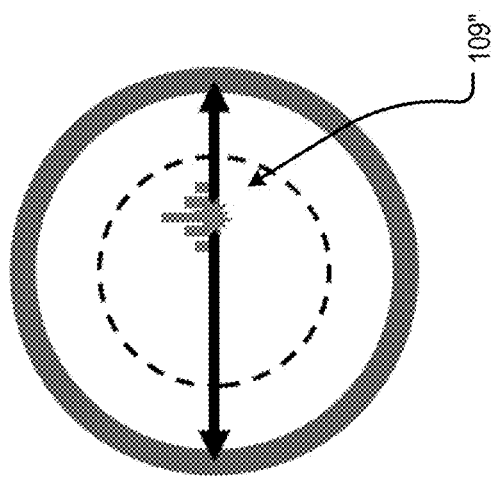
FIG. 1C is an illustration of an estimation of an annihilation event according to time-of-flight (TOF) PET methodologies.
Figure 1B:
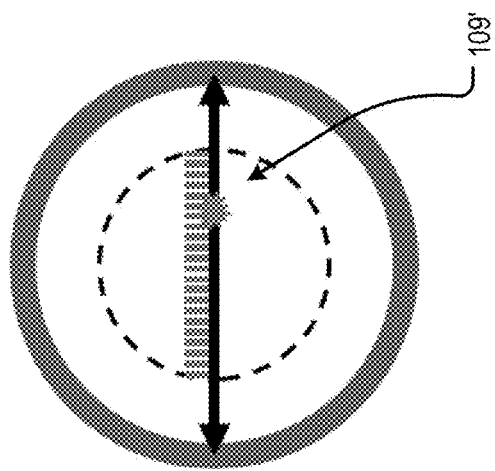
FIG. 1B is an illustration of an estimation of an annihilation event according to convention PET methodologies.
Figure 1A:
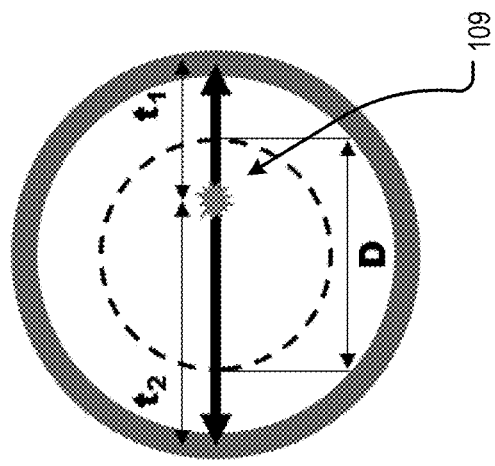
FIG. 1A is an illustration of a true annihilation point, as depicted within a positron emission tomography (PET) imaging system.

The above introduction is illustrated in FIG. 1A through FIG. 1C of the Drawings. In FIG. 1A, $t_1$ and $t_2$ reflect an amount of time for each of two photons generated at a true annihilation point 109 to reach respective detectors of the PET detector ring, where D indicates a distance, or diameter, occupied by a patient. Conventional PET systems, introduced above, cannot discern the values of $t_1$ and $t_2$ with sufficient resolution and, therefore, must rely on image reconstruction that approximates the location of the annihilation event assuming an equal likelihood that the annihilation event took place at each location along a LOR. This equal probability is illustrated in FIG. 1B, wherein the approximate location of the annihilation event 109' has an equal probability of being at any position across a length D of the patient. Of course, in view of FIG. 1A, it is unlikely for the conventional approach of FIG. 1B to be appropriate for all PET systems and all patients, especially as sizes of patients can widely vary. TOF PET, as in FIG. 1C, allows for measurement of $t_1$ and $t_2$ with sufficient timing resolution, therefore enabling approximation of the annihilation point 109" by use of a TOF kernel during image reconstruction. As would be understood by one of ordinary skill in the art, it can be appreciated that the effective signal-to-noise ratio (SNR) gain for TOF PET as compared to non-TOF PET relates to both the timing resolution of the scanner ($\Delta t$) and the size of the scanned subject (D). To this end, $$SNR_{gain} \propto \sqrt{\frac{D}{c\Delta t/2}},$$

where c is the speed of light. Surti provides an informative review of TOF PET and non-TOF PET that is relevant herein (Surti, Suleman, "Update on Time-of-Flight PET Imaging", January 2015, The Journal of Nuclear Medicine, Vol. 56, No. 1).

The SNR gain increases with patient size, D, which is beneficial understanding that, in non-TOF PET, an increasing patient size (D) is likely to increase the number of locations wherein an annihilation event is possible, thus degrading image quality.

When TOF information is available, a Gaussian distribution can be used to predict the location of the annihilation event, as shown in FIG. 1C. Of course, because the time resolution of PET systems is traditionally considered to be generally uniform over all the LORs, TOF kernels applied to image reconstruction are typically a single, averaged time resolution value for all the LORs.

Figure 2A:
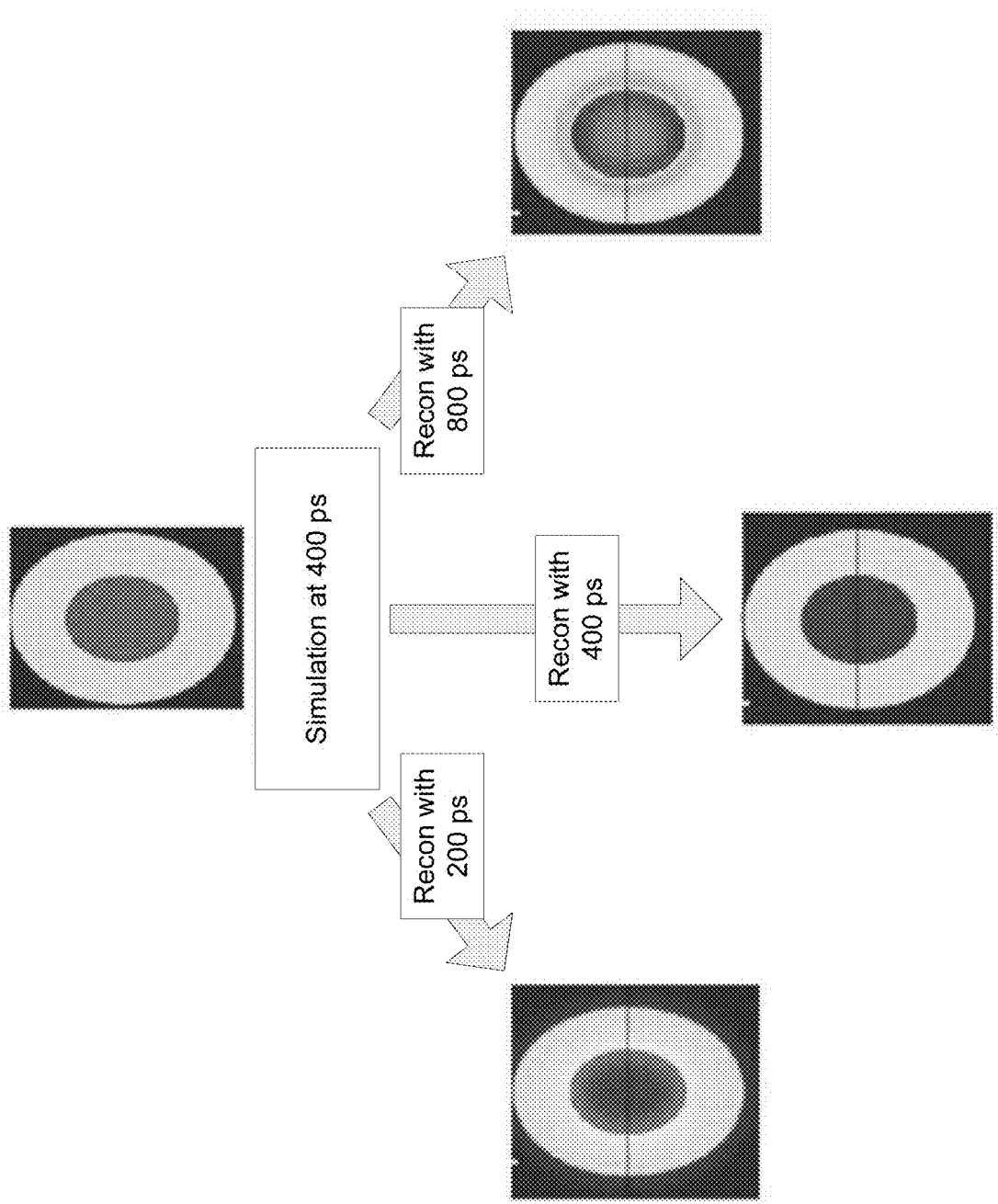
FIG. 2A is a flow diagram illustrating PET image reconstructions performed according to varying TOF kernel widths.

This generalization, though common, oversimplifies the importance of using accurate TOF information to model the system. An incorrect TOF kernel, or TOF kernel width, can lead to, among other things, artifacts within images reconstructed thereon. For instance, TOF kernel widths that are too small can lead to reconstructions with reduced contrast and unrestored edges, while TOF kernel widths that are too large can lead to decreased background uniformity. As shown in FIG. 2A, and given data simulated at 400 ps timing resolution, a smaller kernel width (e.g., 200 ps) will push activity to concentrate at the center of the reconstructed image while a larger kernel width (e.g., 800 ps) will push activity to concentrated towards the edge of the reconstructed image. Only a correctly chosen TOF kernel width (e.g., 400 ps), which may not equal an average of timing resolutions, generates a correct activity distribution. FIG. 2A is adapted from Vandenberghe et al. EJNMMI Physics (2016) 3:3.

Figure 2B:
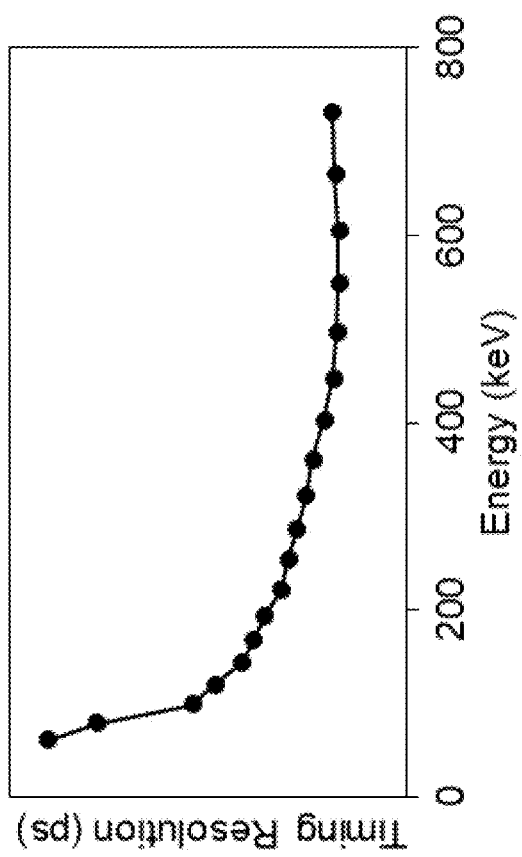
FIG. 2B is a graphical illustration of timing resolution dependence on energy deposition, according to an embodiment of the present disclosure.
Figure 3B:
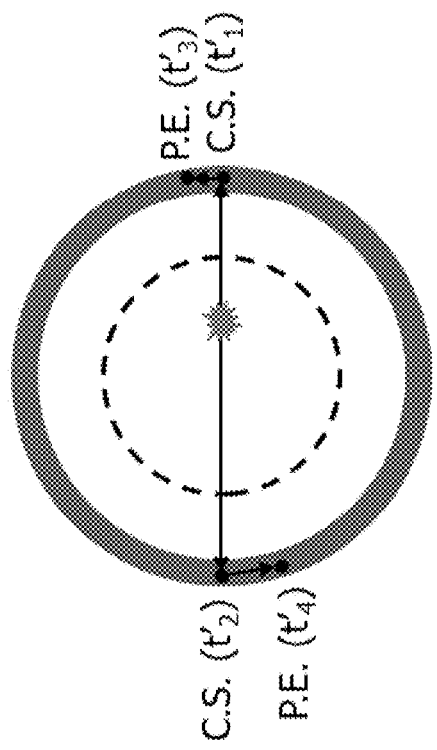
FIG. 3B is an illustration of an annihilation event wherein at least one of the generated gamma rays interacts with more than one gamma ray detector.
Figure 3A:
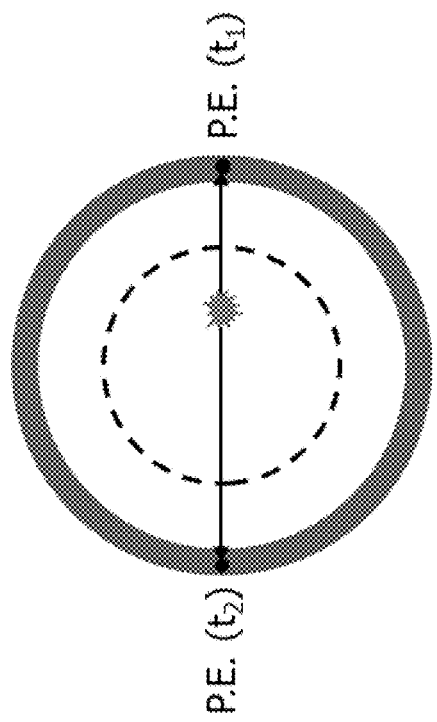
FIG. 3A is an illustration of an annihilation event wherein each generated gamma ray interacts with only one gamma ray detector.

In view of the above, it should be further considered that timing resolution of PET instrumentation depends on the amplitude of the signal detected, as in FIG. 2B. Therefore, the timing resolution depends on the energy of the gamma ray hitting each PET detector. The higher the gamma ray energy, the better (i.e., smaller) the timing resolution. In the case of PET imaging systems, this ideal scenario may be the case when each gamma ray deposits all of its energy within a single PET detector, as shown in FIG. 3A. This event is known as a photoelectric (PE) event. However, not all interactions between gamma rays and scintillators of PET detectors are photoelectric events. In fact, in cases where less than 511 keV of energy are deposited upon a first interaction, the first interaction is referred to as a Compton scattering (CS) event. As shown in FIG. 3B, CS events result in each gamma ray only depositing part of the 511 keV at the scattering point, the gamma ray with reduced energy continuing to travel inside the scintillator until it interacts, again, with the scintillator or leaves the scintillator. The second interaction may be a CS event or a PE event.

Coincidence events like that illustrated in FIG. 3A generate the best timing resolution as both gamma rays generate the largest signals. In the case of FIG. 3B, however, four photodetectors detect scintillation photons as a result of interactions with gamma rays and all signals have smaller amplitude than those of FIG. 3A. Thus, the timing resolution of the interactions of FIG. 3B is degraded, as each generated gamma ray interacts first by a CS event and then by either of a CS event or a PE event. Further to the above, the event described for each gamma ray in FIG. 3B may also be the case for only one of the two generated gamma rays. This mixed event scenario, wherein one photon results in a single event and the other photon results in a multiple interaction event, must also be considered.

PET system designs, including non-TOF systems and TOF systems, do not separate the various scenarios of photon interaction described above with respect to FIG. 3A and FIG. 3B. As discussed, an overall timing resolution, reflective of all kinds of events, is instead calculated. However, for the events illustrated in FIG. 3A and FIG. 3B, wherein one or both of the gamma rays may have multiple interactions with scintillators of the PET detectors, a uniform timing resolution, and thus TOF kernel width, may overshoot or undershoot, resulting in artifacts in image reconstruction.

Thus, according to an embodiment of the present disclosure, a PET system having a dynamic TOF kernel is required for accurate image reconstruction and consideration of the myriad events possible in PET image acquisition. To this end, detector interactions associated with coincidence events (i.e., two gamma rays generated from an annihilation event) need to be evaluated based on the number of times, and with what energy, they each interact with the PET detectors.

Notably, this approach exploits recent advances in PET detector module design, which allow for measurement of energy and timing of scintillation light from each crystal pixel in the crystal array of the PET detector. In this way, it is possible to distinguish between different interaction scenarios when the CS event and the PE event occur in different crystals.

According to an embodiment, annihilation events, or interaction scenarios, can be generally defined as three types of events. A first group, referred to herein as a single-crystal group, includes annihilation events where both gamma rays (or singles) interact with the PET detectors as PE events (i.e., only once), depositing all of their energy in one location. A second group, referred to herein as a multi-crystal group, includes annihilation events where both of the two gamma rays (or singles) interact with the PET detectors as at least one CS event and a PE event or as at least two CS events (i.e., at least twice). A third group, referred to herein as a mixed-crystal group, includes annihilation events where only one of the two gamma rays (or singles) interacts with the PET detectors as a PE event (i.e., only once) and the other one of the two gamma rays (or singles) interacts with the PET detectors as at least one CS event and a PE event or as at least two CS events (i.e., at least twice). Thus, for events within each group definition, different TOF kernel widths can be used during image reconstruction.

In an example, a timing resolution of the first group can be defined as $\Delta t_1$. Timing resolutions for the second group and the third group can be based on the number of interactions of the gamma rays with the scintillators of the PET detectors. With regard to the second group, and assuming each scattered one of the gamma ray pair only interacts twice with the PET detectors, a timing resolution can be defined as $t_2$. With regard to the third group, and assuming one gamma ray of the gamma ray pair deposits energy in a PE event and the other gamma ray of the gamma ray pair is scattered and only interacts with the PET detectors twice, a timing resolution can be defined as a convolution of the first timing resolution, $\Delta t_1$, and the second timing resolution, $\Delta t_2$, as $$\Delta t_3 = \sqrt{\frac{\Delta t_1^2 + \Delta t_2^2}{2}}.$$

Of course, the timing resolutions are not limited to these definitions, as changes in the number of crystal interactions amongst the scattered gamma rays, and thus changes in energy deposited, will change the timing resolution of the PET system. For instance, in a multi-crystal event (i.e., wherein at least three interactions have occurred between the gamma ray pair), variable amounts of energy may be deposited on each crystal based on CS event kinematics. Appreciating the timing resolution is related to energy deposition, it can be appreciated that $\Delta t_2$ and $\Delta t_3$ can be further divided into finer subgroups according to deposited energy levels. In an example, corresponding timing resolutions may be determined according to a look up table developed based on energy deposition, number of photon interactions, timing resolutions, and the like. In another example, corresponding timing resolutions may be determined according to an evaluation of a function defining the relationship between energy deposition, number of photon interactions, timing resolutions, and the like.

In a general form, the TOF kernel for image reconstruction can be determined event by event with the following functions—

$$\Delta t = \sqrt{\Delta t_a^2 + \Delta t_b^2}, \text{ where}$$

$$\Delta t_a^2 = f(E_1, E_2, E_3, \ldots, E_i, \ldots, E_M), \text{ and}$$

$$\Delta t_b^2 = f(E_1, E_2, E_3, \ldots, E_j, \ldots, E_N),$$

where $\Delta t_a$ is the timing resolution for the first of the paired gamma rays hitting the PET detectors, $E_i$ is the measured energy for the first gamma ray deposits on each crystal, M is the total number of crystals the first gamma ray hits, $\Delta t_b$ is the timing resolution for the second of the paired gamma rays hitting the PET detectors, $E_j$ is the measured energy for the second gamma ray deposits on each crystal, and N is the total number of crystals the second gamma ray hits. The function of calculating $\Delta t_a$ and $\Delta t_b$ can be determined by the calibration process, which can be an empirical formula or a look-up table.

The system and methods described herein eliminate the inaccuracy of extracting a single timing resolution for all coincidence events, as in previous PET systems. The methods herein provide improved accuracy in defining the timing resolution for each event observed by a PET system. This increasingly accurate timing resolution information reduces artifacts during image reconstruction, thereby achieving better image quality.

The system and methods herein utilize different TOF kernels (i.e. different TOF kernel widths) for coincidence events with different timing resolutions. Matching TOF kernel widths to corresponding timing resolutions will improve the PET image by reducing artifacts caused by using a single TOF kernel.

According to an embodiment, the present disclosure describes a method of using a dynamically-adjustable TOF kernel width in PET image reconstruction. Since all data are acquired in list-mode format, the timing resolution can either be determined event by event or be determined LOR by LOR. The dynamic TOF kernel may be used in list-mode PET image reconstruction if the timing resolution is determined event by event. If the timing resolution is determined LOR by LOR, the dynamic TOF kernel may be used in list-mode image reconstruction or, following grouping of the list-mode data by LOR to form a sinogram, in sinogram-based image reconstruction.

In an embodiment, the present disclosure describes a method of determining a timing resolution of a PET scanner event by event. The timing resolution may be determined by the energies of the gamma ray pair for each coincidence event. This can be determined with an understanding that timing resolution changes can also be caused by other factors, such as location of gamma ray interaction, which provides a LOR dependent timing resolution.

In an embodiment, the dynamic TOF kernel methods described herein can be applied to other imaging modalities to improve image quality.

In an embodiment, the method can also be implemented by splitting data into groups with different TOF kernel widths, reconstructing images for each group, and then combining the reconstructed images thereafter.

Figure 4:
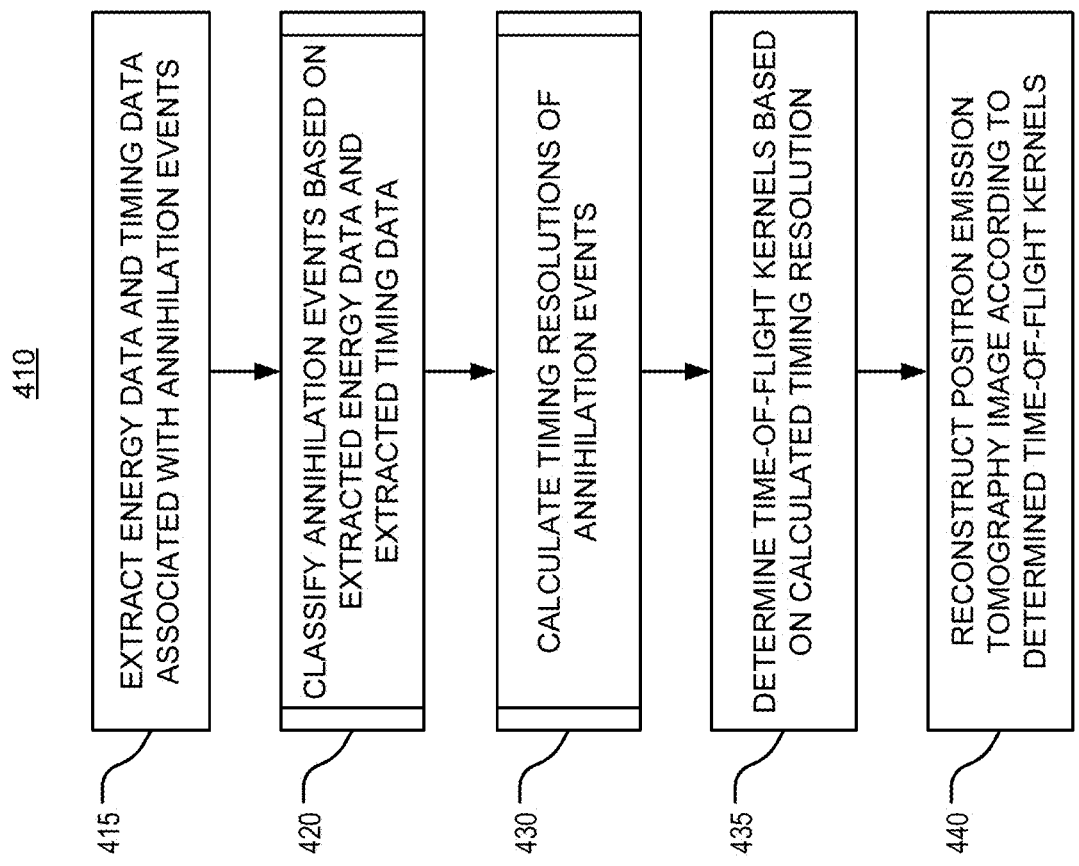
FIG. 4 is a flow diagram of a method for reconstructing a PET image, according to an exemplary embodiment of the present disclosure.

The above introduction and description will now be described with reference to the flow diagram of FIG. 4. The flow diagram of FIG. 4 describes method 410. Method 410 includes steps and sub processes that process extracted energy data and extracted timing data in order to reconstruct a PET image using dynamically-adjusted TOF kernels.

First, at step 415 of method 410, energy data and timing data, which have underlying associations with annihilation events, can be extracted from data obtained from a PET acquisition. In an embodiment, the data obtained from the PET acquisition are arranged chronologically and are not pre-processed according to event data. In another embodiment, which may be more commonly implemented, the data obtained from the PET acquisition may be list-mode data that is arranged event by event according to associated energy data and timing data.

At sub process 420 of method 410, and assuming the data is acquired as list-mode data, the extracted energy data and extracted timing data can be processed, for each annihilation event, to identify associated PE events and CS events and to classify the annihilation event based on the number of crystal interactions of each of the two gamma rays generated by the annihilation events. Sub process 420 will be described in greater detail with reference to FIG. 5A.

The classified annihilation event(s) generated at sub process 420 of method 410 can be used at sub process 430 of method 410 to calculate timing resolutions of each of the classified annihilation event(s). Though sub process 430 of method 410 will be described in greater detail with reference to FIG. 5B, it can be appreciated that the calculated timing resolutions are based on comparisons of, at least, the event classification, to tabular structures, timing resolution models, and the like.

The timing resolutions calculated at sub process 430 of method 410 can be used at step 435 of method 410 to determine TOF kernels for each annihilation event. In an embodiment, a width of the TOF kernel for each annihilation event is determined to be equivalent to the calculated timing resolution for each annihilation event. In another embodiment, a width of the TOF kernel for each annihilation event may be determined according to the calculated timing resolution for each annihilation event and system-dependent hardware factors.

At step 440 of method 410, the determined TOF kernels can be used for image reconstruction of the PET acquisition data whence the energy data and timing data were extracted. The image reconstruction may be list-mode-based image reconstruction or, following grouping of the list-mode data by LOR to generate a sinogram, sinogram-based image reconstruction. The image reconstruction may be performed by analytical reconstruction techniques, iterative reconstruction techniques, and the like. The iterative reconstruction techniques may include Maximum Likelihood Expectation Maximization (MLEM), ordered subsets Expectation Maximization (OSEM), algebraic reconstruction techniques (ART), and maximum a posteriori (MAP) reconstruction, among others.

Figure 5A:
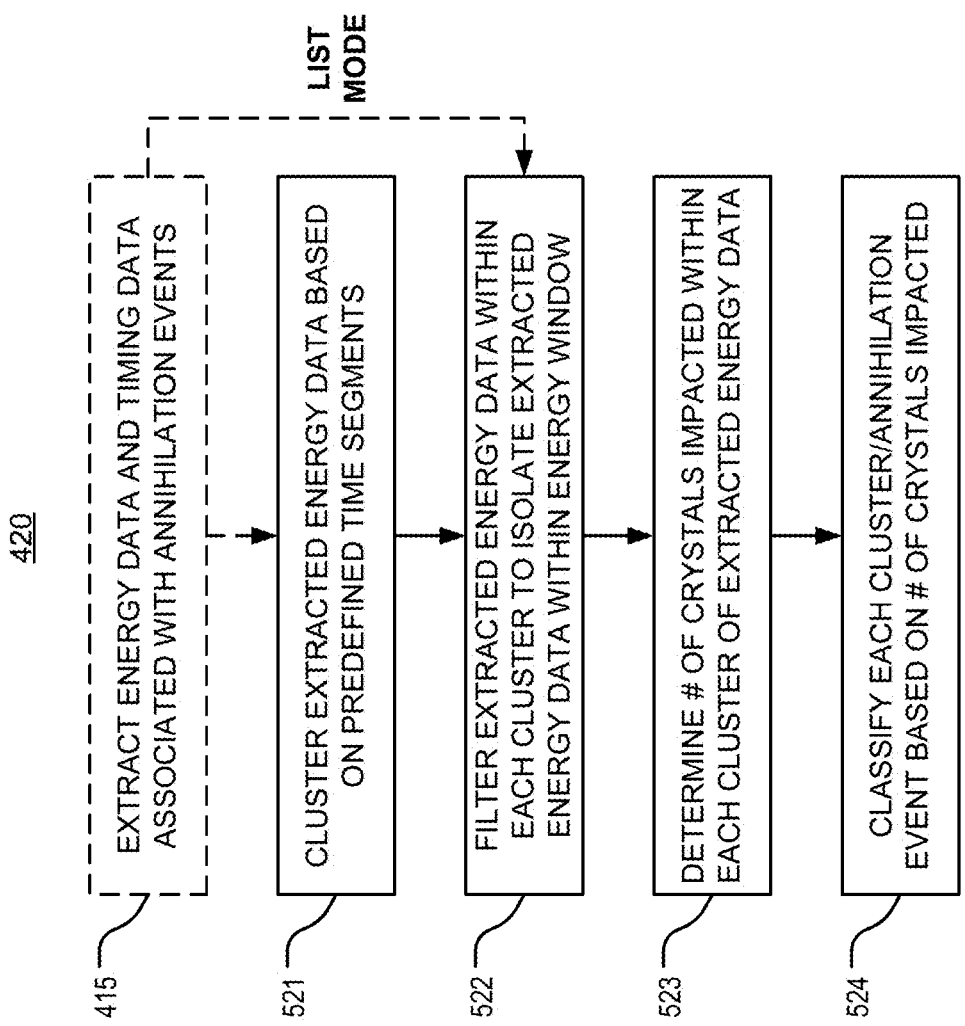
FIG. 5A is a flow diagram of a sub process of a method for reconstructing a PET image, according to an exemplary embodiment of the present disclosure.

Sub process 420 of method 410 will now be further described with reference to FIG. 5A. Initially, sub process 420 includes receiving the extracted energy data and the extracted timing data corresponding to the PET acquisition data.

According to an embodiment, wherein the PET acquisition data is not acquired as list-mode data, sub process 420 proceeds to step 521, where data entries are clustered based on a predefined time segment corresponding to a known window of time associated with an annihilation event. In other words, gamma rays, and their detector interactions, that emanate from a single annihilation event should be grouped together for analysis. In an embodiment, this approach permits LOR by LOR evaluation.

In an embodiment, the window of time, or the predefined time segment, may be a single value for analysis of the entire acquired dataset. The predefined time segment may be 2 nanoseconds (ns), 3 ns, 4 ns, and the like. In an example, the predefined time segment is 3 ns. Each predefined time segment of data may have two or more energy data entries corresponding to detected interactions of the pair of gamma rays with gamma ray detectors of the PET system. These detected interactions, or counts, may include extraneous counts and data entries of a range of energy levels. The extracted energy data clustered at step 521 of sub process 420 may be provided to step 522 of sub process 420.

According to an embodiment, wherein the PET acquisition data is acquired in list-mode, energy data and timing data, already recorded event by event, can be directly extracted and then provided to step 522 of sub process 420.

Figure 6:
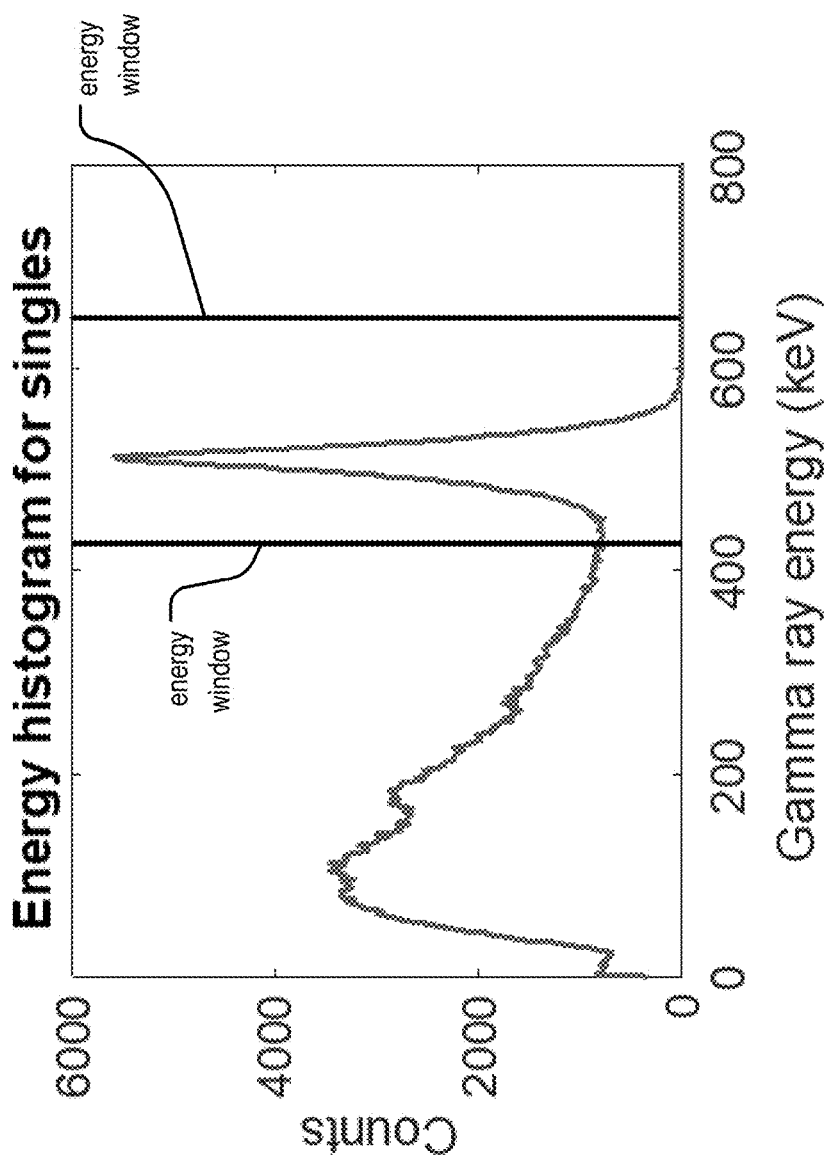
FIG. 6 is an energy histogram and energy window for detected gamma rays, according to an exemplary embodiment of the present disclosure.

By either of the above-described processes, step 522 of sub process 420 includes isolating a preferred energy window of the extracted energy data for each gamma ray, or single, within each cluster, or pair, of annihilation event data. The preferred energy window can be applied to a sum of extracted energy data for each single. Isolating the preferred energy window may include application of an energy filter, as illustrated in FIG. 6, to reduce the data set to those interactions likely to be associated with the annihilation event. In an example, the energy window, or energy filter, may be a window of between 425 keV and 650 keV, appreciating that positron annihilation produces two-coincident 511 keV gamma rays.

Figure 7:
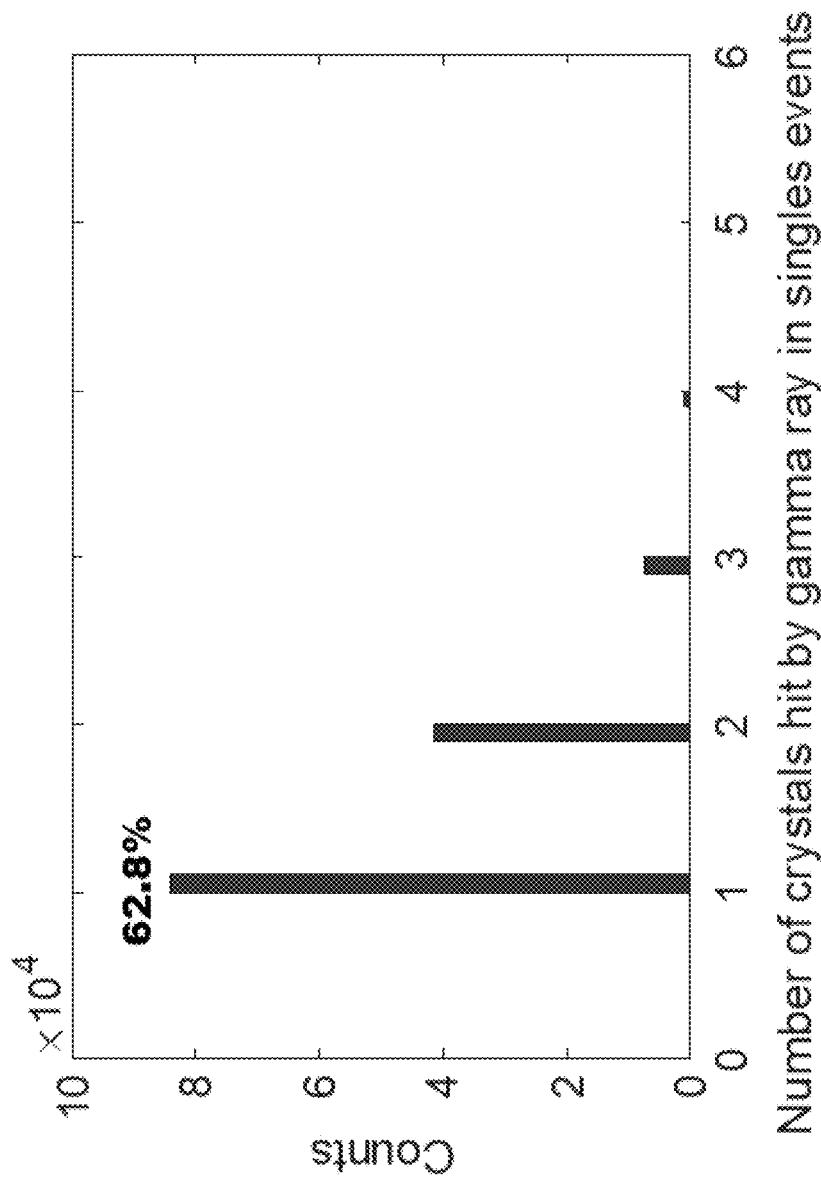
FIG. 7 is a graphical illustration of, for all annihilation events, a number of gamma ray detectors impacted by a single gamma ray, according to an exemplary embodiment of the present disclosure.

At step 523 of sub process 420, the filtered energy data can be evaluated to determine the number of detector crystal interactions by each single associated with each annihilation event. Such an evaluation can be determined by assessing the number of counts for each single of each 'pair' of associated gamma rays within the filtered energy data. Excepting anomalies, 'pair' data may include at least two counts where each single deposits all of its energy within a single crystal hit as a PE event. 'Pair' data may include three or more counts, as well, depending on CS events and interactions of singles with detector crystals. In fact, as illustrated in FIG. 7, which provides a histogram of number of detector crystals hit by all singles that pass, individually or cumulatively, the 425-650 keV window, a majority (62.8%) of singles, or gamma rays, interact only once with a detector crystal. However, it can also be appreciated from FIG. 7 that nearly 40% of gamma rays result in multi-crystal events, wherein at least one CS event is observed.

As described above, and according to an embodiment, annihilation events can be generally defined as different types of events. In the instance there are only three types, or groups, of events, they can be defined as follows. A first group is a single-crystal group, where both gamma rays interact with a respective one of the crystals of the PET detectors as PE events (i.e., only once). A second group is a multi-crystal group, where both of the two gamma rays interact with multiple crystals as at least one CS event and a PE event or as at least two CS events (i.e., at least twice). A third group is a mixed-crystal group, where only one of the two gamma rays interacts with a single crystal of the PET detectors as a PE event (i.e., only once) while the other one of the two gamma rays interacts with multiple crystals of the PET detectors as at least one CS event and a PE event or as at least two CS events (i.e., at least twice).

Accordingly, at step 524 of sub process 420, and having determined the number of crystal interactions within each cluster of extracted energy data at step 523 of sub process 420, each cluster, or annihilation event, can be classified according to a number of crystal interactions (i.e., the number of detector crystals, or scintillator crystals, within a crystal array of each gamma ray detector that are hit).

In an embodiment, if only two counts are registered within the annihilation event, the annihilation event can be classified as a single-crystal event. In an embodiment, if more than two counts are registered, the extracted energy data of the counts can be assessed to determine how the energy from two gamma rays generated by the annihilation event was deposited. For instance, if four counts are registered, the underlying energy data may indicate that there was one 511 keV hit, corresponding to a PE event of one of the gamma rays, and that the other three counts are associated with a single gamma ray interacting with multiple detector crystals. In another instance, four counts may be registered and may indicate that each gamma ray of the annihilation event interacted with multiple detector crystals of the gamma ray detectors as a CS event and, subsequently, as either one of a CS event or a PE event. In any of the instances described above, the event can be classified as one of a single-crystal group, a mixed-crystal group, and a multi-crystal group, based on the number of counts registered and the energy data associated therewith.

Of course, according to an embodiment, the classifications of the interactions are not limited to only the three groups, or types, of events described above. In other instances, while the first group may be defined as a single-crystal group (i.e. each gamma ray deposits within single crystals as a PE event, only), the second group and the third group may be further granulated based on the number of detector crystals hit. For instance, in a type of "mixed-crystal event" one gamma ray may deposit in a PE event within a single detector crystal while the other gamma ray may interact with multiple detector crystals as two CS events and, ultimately, a PE event. By acknowledging variations of mixed-crystal events and multi-crystal events, and accounting for them, improved image reconstructions are possible, as will be described below.

Figure 5B:
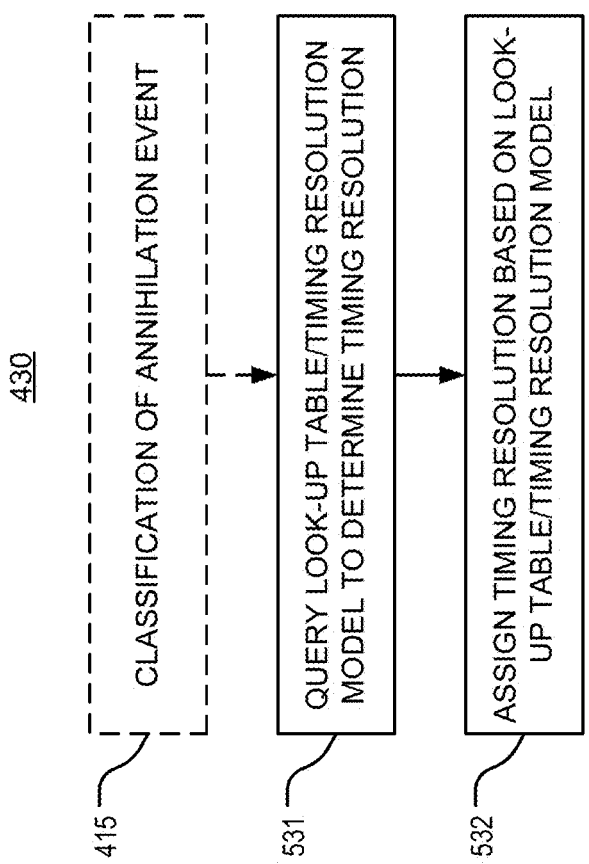
FIG. 5B is a flow diagram of a sub process of a method for reconstructing a PET image, according to an exemplary embodiment of the present disclosure.

Having classified each event, timing resolutions can be calculated for each event according to sub process 430 of method 410, described in further detail with respect to FIG. 5B and in view of FIG. 8.

At step 531 of sub process 430, annihilation event classifications obtained from step 415 can be used to determine a timing resolution of the annihilation event. To this end, the classification can be used to query one of a look up table (LUT), a timing resolution model, and the like, in order to determine a timing resolution that should be assigned to the annihilation event and used during image reconstruction.

As described above, a timing resolution of the first group can be defined as $\Delta t_1$. In an example, $\Delta t_1$ may be 100 picoseconds (ps), 200 ps, and 300 ps, as appropriate. Timing resolutions for the second group and the third group can be based on the number of interactions of the photons with detector crystals of the PET detectors. With regard to the second group, and assuming each scattered photon of the gamma ray pair only interacts with two detector crystals of the PET detectors, a timing resolution can be defined as $\Delta t_r$. $\Delta t_2$ may be 600 ps, 700 ps, or 800 ps. With regard to the third group, and assuming one gamma ray of the gamma ray pair deposits energy in a PE event within a single detector crystal and the other gamma ray of the gamma ray pair is scattered, interacting with two detector crystals of the PET detectors, a timing resolution can be defined as a convolution of the first timing resolution, $\Delta t_1$, and the second timing resolution, $\Delta t_r$, as $$\Delta t_3 = \sqrt{\frac{\Delta t_1^2 + \Delta t_2^2}{2}}.$$

Having evaluated the LUT, the timing resolution model, or the like, the classification associated timing resolution can then be assigned to the annihilation event data at step 532 of sub process 430. Thus, the timing resolution can be used at step 435 of method 410 to determine the TOF kernel width prior to image reconstruction at step 440 of method 410.

According to an embodiment, and as introduced above, the classifications of the interactions are not limited to only three groups. While the first group may be defined as a single-crystal group, the second group and the third group may be further granulated based on the number of crystals hit. For instance, in a type of "mixed-crystal event" one gamma ray, or single, of a pair of singles may deposit in a PE event within a single detector crystal (single crystal single), while the other gamma ray, or single, of the pair of singles may interact with multiple detector crystals as two CS events and, ultimately, a PE event (multi-crystal single). By acknowledging the other single interacts with three crystals, a prescribed timing resolution for the event can be tuned to the specific interaction and deposited energies thereof. It can be appreciated that a timing resolution of a multi-crystal single interacting with three crystals will be higher (i.e., poorer) than a multi-crystal single interacting with two crystals, as the energy of each hit is likely to be lower assuming the final hit is a PE event. Accordingly, the timing resolution for the event will reflect these intricacies.

In an embodiment, deeper granularity of the energy data in classifying the events can be extended to determination of an appropriate timing resolution thereof. For instance, instead of identifying only three timing resolutions based on three classification groups, a myriad number of timing resolutions may be available and correspond to different event classifications that vary with the number of hits, by gamma ray, and the energy deposited at the crystal with each hit. A LUT or other timing resolution model can then include additional information that populates the model, thus providing a more accurate timing resolution.

Figure 9:
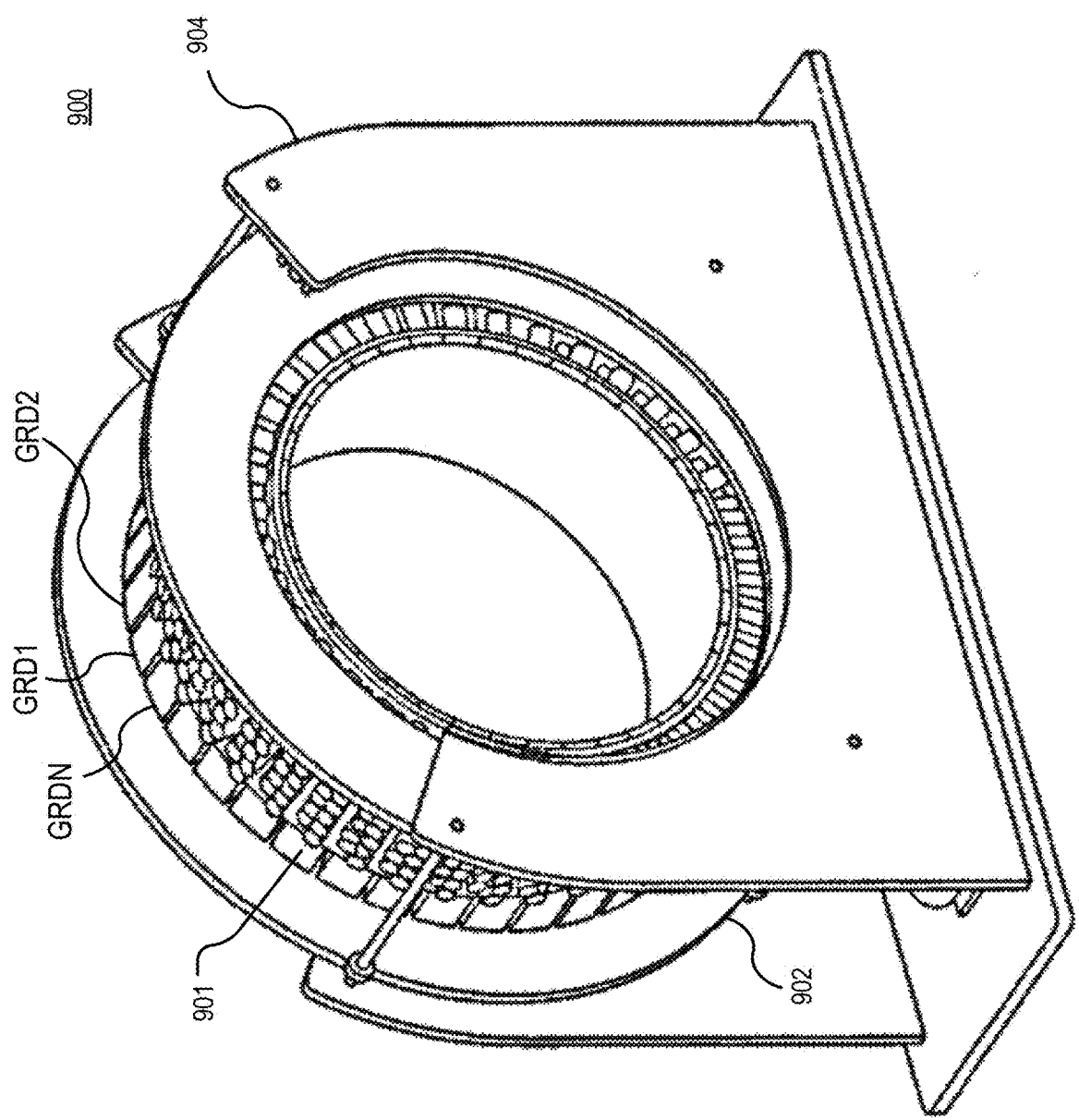
FIG. 9 is an illustration of a perspective view of a PET scanner, according to an exemplary embodiment of the present disclosure.
Figure 10:
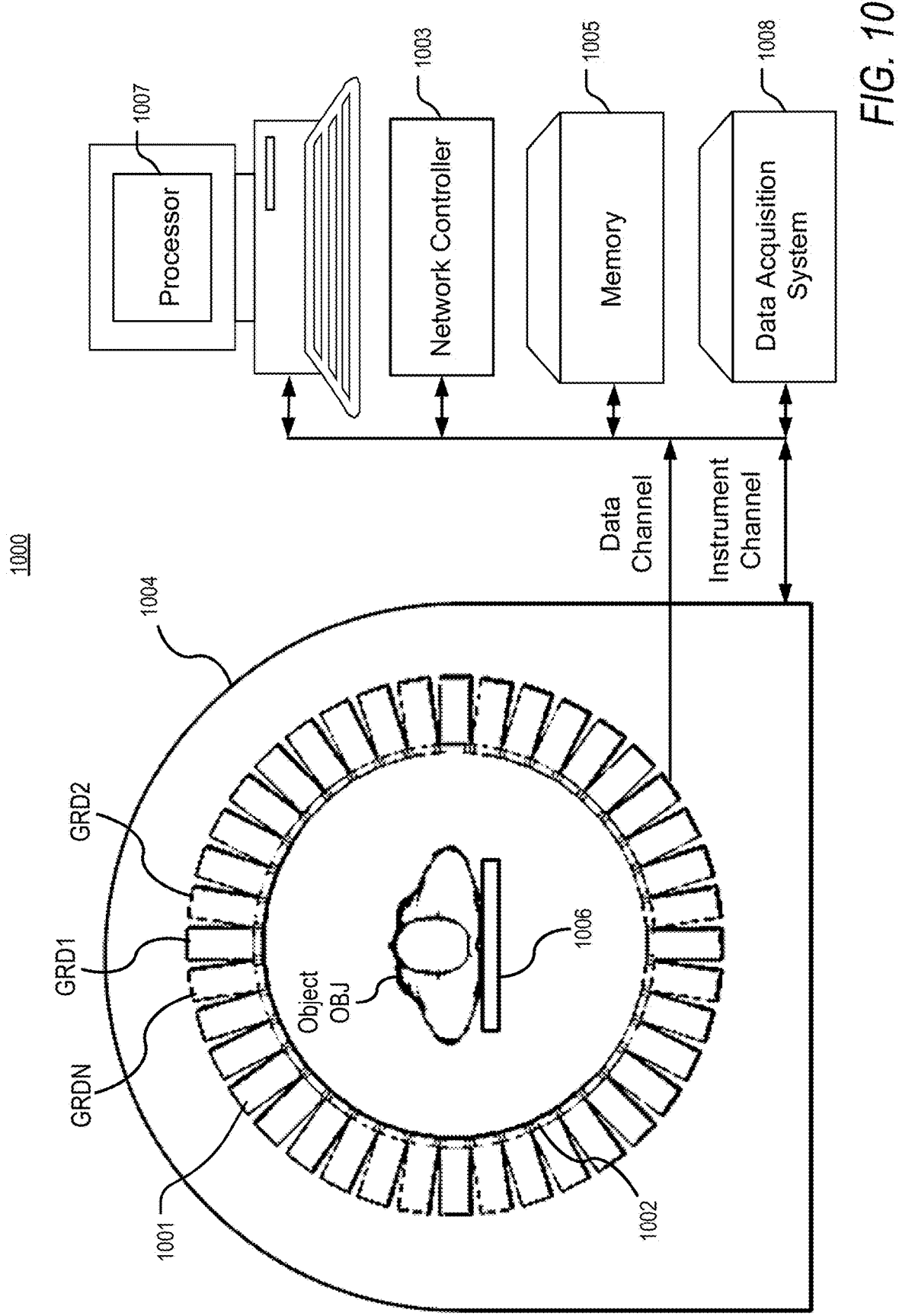
FIG. 10 is a schematic of a PET scanner and associated hardware, according to an exemplary embodiment of the present disclosure.

The above methods can be implemented within a PET scanner, as shown in FIG. 9 and FIG. 10. Therefore, FIG. 9 and FIG. 10 show a PET scanner 900 including a number of gamma-ray detectors (GRDs) 901 (e.g., GRD1, GRD2, through GRDN) that are each configured as rectangular detector modules. According to one implementation, each PET detector ring, which forms a circular bore 902 about a gantry 904, includes 40 GRDs. In another implementation, there are 48 GRDs, the higher number of GRDs being used to create a larger bore size for the PET scanner 900. The GRDs include scintillator crystal arrays for converting the gamma rays into scintillation photons (e.g., at optical, infrared, and ultraviolet wavelengths), which are detected by photodetectors. Each GRD can include a two-dimensional array of individual detector crystals, which absorb gamma radiation and emit scintillation photons. The scintillation photons can be detected by a two-dimensional array of silicon photomultipliers (SiPMs) that are also arranged in the GRD. There is a one-to-one correspondence between the crystals and the photodetectors. A light guide can be disposed between the array of detector crystals and the SiPMs. Further, each GRD can include a number of SiPMs of various sizes, each of which is arranged to receive scintillation photons from a plurality of detector crystals. Each SiPM can produce an analog signal that indicates when scintillation events occur, and an energy of the gamma ray producing the detection event.

FIG. 10 shows a schematic view of a PET scanner system having GRDs arranged to detect gamma-rays emitted from an object OBJ. The GRDs can measure the timing, position, and energy corresponding to each gamma-ray detection. In one implementation, the gamma-ray detectors are arranged in a PET detector ring, as shown in FIG. 9 and FIG. 10, and as described herein. It can be appreciated that the single PET detector ring of FIG. 10 can be extrapolated to include any number of PET detector rings along an axial length of the PET scanner. The detector crystals can be scintillator crystals, which have individual scintillator elements arranged in a two-dimensional array and the scintillator elements can be any known scintillating material.

FIG. 10 shows an example of the arrangement of the PET scanner 1000, in which the object OBJ to be imaged rests on a table 1006 and the GRD modules GRDI through GRDN are arranged circumferentially around the object OBJ and the table 1006. The GRDs may comprise a PET detector ring and may fixedly-connected to a circular bore 1002 that is fixedly-connected to a gantry 1004. The gantry 1004 houses many parts of the PET scanner. The gantry 1004 of the PET scanner also includes an open aperture, defined by the cylindrical bore 1002, through which the object OBJ and the table 1006 can pass, and gamma-rays emitted in opposite directions from the object OBJ due to an annihilation event can be detected by the GRDs and timing and energy information can be used to determine coincidences for gamma-ray pairs.

In FIG. 10, circuitry and hardware is also shown for acquiring, storing, processing, and distributing gamma-ray detection data. The circuitry and hardware include a processor 1007, a network controller 1003, a memory 1005, and a data acquisition system (DAS) 1008. The PET imager also includes a data channel that routes detection measurement results from the GRDs to the DAS 1008, the processor 1007, the memory 1005, and the network controller 1003. The DAS 1008 can control the acquisition, digitization, and routing of the detection data from the detectors. In one implementation, the DAS 1008 controls the movement of the table 1006. The processor 1007 performs functions including pre-reconstruction processing of the detection data, image reconstruction, and post-reconstruction processing of the image data, as appropriate.

According to an embodiment, the processor 1007 of the PET scanner 900, 1000 of FIG. 9 and FIG. 10 can be configured to perform method 410, as described herein. The processor 1007 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory 1005 can be a hard disk chive, CD-ROM drive, DVD drive, FLASH drive, RAM, ROM or any other electronic storage known in the art. The memory 1005 may be non-volatile, such as ROM, EPROM, EEPROM or FLASH memory. The memory 1005 can also be volatile, such as static or dynamic RAM, and a processor, such as a microcontroller or microprocessor, may be provided to manage the electronic memory as well as the interaction between the FPGA or CPLD and the memory.

Alternatively, the CPU in the processor 1007 can execute a computer program including a set of computer-readable instructions that perform method 410 described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

In one implementation, the PET scanner may include a display for displaying a reconstructed image and the like. The display can be an LCD display, CRT display, plasma display, OLED, LED or any other display known in the art.

The network controller 1003, such as an Intel Ethernet PRO network interface card from Intel Corporation of America, can interface between the various parts of the PET imager. Additionally, the network controller 1003 can also interface with an external network. As can be appreciated, the external network can be a public network, such as the Internet, or a private network such as an LAN or WAN network, or any combination thereof and can also include PSTN or ISDN sub-networks. The external network can also be wired, such as an Ethernet network, or can be wireless such as a cellular network including EDGE, 3G, 4G, and 5G wireless cellular systems. The wireless network can also be WiFi, Bluetooth, or any other wireless form of communication that is known.

Obviously, numerous modifications and variations are possible in light of the above teachings. It is therefore to be understood that within the scope of the appended claims, the invention may be practiced otherwise than as specifically described herein.

Embodiments of the present disclosure may also be as set forth in the following parentheticals.

(1) An apparatus for reconstructing a positron emission tomography image, comprising processing circuitry configured to extract, from raw data obtained from a positron emission tomography scanner, energy data and timing data associated with a plurality of annihilation events, the extracted energy data and the extracted timing data for each annihilation event corresponding to interactions between each of a pair of gamma rays generated by each annihilation event and one or more gamma ray detectors of the positron emission tomography scanner, classify each annihilation event based on respective extracted energy data and respective extracted timing data, calculate a timing resolution for each annihilation event based on the classification, determine, for each annihilation event and based on the calculated timing resolution of the annihilation event, a width of a time-of-flight kernel, and reconstruct, by processing circuitry, the positron emission tomography image based on the obtained raw data from the positron emission tomography scanner and the determined width of the time-of-flight kernel associated with each annihilation event.

(2) The apparatus according to (1), wherein the processing circuitry is further configured to classify each annihilation event by determining, from the respective extracted energy data and the respective extracted timing data, a quantity of the one or more gamma ray detectors impacted by each of the pair of gamma rays generated by the annihilation event.

(3) The apparatus according to either (1) or (2), wherein the processing circuitry is further configured to classify the annihilation event as a single-crystal event, a multi-crystal event, or a hybrid-crystal event based on the determined quantity of the one or more gamma ray detectors impacted by each gamma ray of the pair of gamma rays generated by the annihilation event.

(4) The apparatus according to any one of (1) to (3), wherein the single-crystal event is a photoelectric event, the multi-crystal event is a scattering event, and the hybrid-crystal event is a combination thereof (5) The apparatus according to any one of (1) to (4), wherein the processing circuitry is further configured to, when the classification indicates an annihilation event is a hybrid-crystal event, calculate the timing resolution by a convolution of a timing resolution associated with a single-crystal event and a timing resolution associated with a multi-crystal event.

(6) The apparatus according to any one of (1) to (5), wherein each annihilation event includes interactions of gamma rays with the one or more gamma ray detectors during a predetermined time period.

(7) A method for reconstructing a positron emission tomography image, comprising extracting, by processing circuitry and from raw data obtained from a positron emission tomography scanner, energy data and timing data associated with a plurality of annihilation events, the extracted energy data and the extracted timing data for each annihilation event corresponding to interactions between each of a pair of gamma rays generated by each annihilation event and one or more gamma ray detectors of the positron emission tomography scanner, classifying, by the processing circuitry, each annihilation event based on respective extracted energy data and respective extracted timing data, calculating, by the processing circuitry, a timing resolution for each annihilation event based on the classification, determining, by the processing circuitry and for each annihilation event, a width of a time-of-flight kernel, and reconstructing, by the processing circuitry, the positron emission tomography image based on the obtained raw data from the positron emission tomography scanner and the determined width of the time-of-flight kernel associated with each annihilation event.

(8) The method according to (7), wherein the classifying includes, for each annihilation event, determining, by the processing circuitry and from the respective extracted energy data and the respective extracted timing data, a quantity of the one or more gamma ray detectors impacted by each gamma ray of the pair of the gamma rays generated by the annihilation event.

(9) The method according to either (7) or (8), wherein the classifying classifies the annihilation event as a single-crystal event, a multi-crystal event, or a hybrid-crystal event based on the determined quantity of the one or more gamma ray detectors impacted by each of the pair of gamma rays generated by the annihilation event.

(10) The method according to any one of (7) to (9), wherein the single-crystal event is a photoelectric event, the multi-crystal event is a scattering event, and the hybrid-crystal event is a combination thereof.

(11) The method according to any one of (7) to (10), wherein the calculating includes, when the classifying indicates an annihilation event is a hybrid-crystal event, calculate the timing resolution by a convolution of a timing resolution associated with a single-crystal event and a timing resolution associated with a multi-crystal event.

(12) A non-transitory computer-readable storage medium storing computer-readable instructions that, when executed by a computer, cause the computer to perform a method for reconstructing a positron emission tomography image, comprising extracting, from raw data obtained from a positron emission tomography scanner, energy data and timing data associated with a plurality of annihilation events, the extracted energy data and the extracted timing data for each annihilation event corresponding to interactions between each of a pair of gamma rays generated by each annihilation event and one or more gamma ray detectors of the positron emission tomography scanner, classifying each annihilation event based on respective extracted energy data and respective extracted timing data, calculating a timing resolution for each annihilation event based on the classification, determining, for each annihilation event and based on the calculated timing resolution of the annihilation event, a width of a time-of-flight kernel, and reconstructing the positron emission tomography image based on the obtained raw data from the positron emission tomography scanner and the determined width of the time-of-flight kernel associated with each annihilation event.

(13) The non-transitory computer-readable storage medium according to (12), wherein the classifying includes, for each annihilation event, determining, from the respective extracted energy data and the respective extracted timing data, a quantity of the one or more gamma ray detectors impacted by each of the pair of gamma rays generated by the annihilation event.

(14) The non-transitory computer-readable storage medium according to either (12) or (13), wherein the classifying classifies the annihilation event as a single-crystal event, a multi-crystal event, or a hybrid-crystal event based on the determined quantity of the one or more gamma ray detectors impacted by each of the pair of gamma rays generated by the annihilation event.

(15) The non-transitory computer-readable storage medium according to any one of (12) to (14), wherein the calculating includes, when the classifying indicates an annihilation event is a hybrid-crystal event, calculate the timing resolution by a convolution of a timing resolution associated with a single-crystal event and a timing resolution associated with a multi-crystal event.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. An apparatus for reconstructing a positron emission tomography image, comprising:
    processing circuitry configured to
        extract, from raw data obtained from a positron emission tomography scanner, energy data and timing data associated with a plurality of annihilation events, the extracted energy data and the extracted timing data for each annihilation event corresponding to interactions between each of a pair of gamma rays generated by each annihilation event and one or more gamma ray detectors of the positron emission tomography scanner,
        classify each annihilation event based on respective extracted energy data and respective extracted timing data,
        calculate a timing resolution for each annihilation event based on the classification,
        determine, for each annihilation event and based on the calculated timing resolution of the annihilation event, a width of a time-of-flight kernel, and
        reconstruct, by processing circuitry, the positron emission tomography image based on the obtained raw data from the positron emission tomography scanner and the determined width of the time-of-flight kernel associated with each annihilation event,
    wherein the processing circuitry is further configured to classify each annihilation event by determining, from the respective extracted energy data and the respective extracted timing data, a quantity of the one or more gamma ray detectors impacted by each of the pair of gamma rays generated by the annihilation event,
    wherein the processing circuitry is further configured to classify the annihilation event as a single-crystal event, a multi-crystal event, or a hybrid-crystal event based on the determined quantity of the one or more gamma ray detectors impacted by each gamma ray of the pair of gamma rays generated by the annihilation event,
    wherein the single-crystal event is a photoelectric event, the multi-crystal event is a scattering event, and the hybrid-crystal event is a combination thereof, and
    wherein the processing circuitry is further configured to. when the classification indicates an annihilation event is a hybrid-crystal event, calculate the timing resolution by a convolution of a timing resolution associated with a single-crystal event and a timing resolution associated with a multi-crystal event.

2. The apparatus according to claim 1, wherein each annihilation event includes interactions of gamma rays with the one or more gamma ray detectors during a predetermined time period.

3. A method for reconstructing a positron emission tomography image, comprising:
    extracting, by processing circuitry and from raw data obtained from a positron emission tomography scanner, energy data and timing data associated with a plurality of annihilation events, the extracted energy data and the extracted timing data for each annihilation event corresponding to interactions between each of a pair of gamma rays generated by each annihilation event and one or more gamma ray detectors of the positron emission tomography scanner;

classifying, by the processing circuitry, each annihilation event based on respective extracted energy data and respective extracted timing data;

calculating, by the processing circuitry, a timing resolution for each annihilation event based on the classification;

determining, by the processing circuitry and for each annihilation event, a width of a time-of-flight kernel; and reconstructing, by the processing circuitry, the positron emission tomography image based on the obtained raw data from the positron emission tomography scanner and the determined width of the time-of-flight kernel associated with each annihilation event, wherein the classifying includes, for each annihilation event:

determining, by the processing circuitry and from the respective extracted energy data and the respective extracted timing data, a quantity of the one or more gamma ray detectors impacted by each gamma ray of the pair of the gamma rays generated by the annihilation event, wherein the classifying classifies the annihilation event as a single-crystal event, a multi-crystal event, or a hybrid-crystal event based on the determined quantity of the one or more gamma ray detectors impacted by each gamma ray of the pair of gamma rays generated by the annihilation event, wherein the single-crystal event is a photoelectric event, the multi-crystal event is a scattering event, and the hybrid-crystal event is a combination thereof, and wherein the calculating includes, when the classifying indicates an annihilation event is a hybrid-crystal event, calculating the timing resolution by a convolution of a timing resolution associated with a single-crystal event and a timing resolution associated with a multi-crystal event.

4. A non-transitory computer-readable storage medium storing computer-readable instructions that, when executed by a computer, cause the computer to perform a method for reconstructing a positron emission tomography image, comprising:

extracting, from raw data obtained from a positron emission tomography scanner, energy data and timing data associated with a plurality of annihilation events, the extracted energy data and the extracted timing data for each annihilation event corresponding to interactions between each of a pair of gamma rays generated by each annihilation event and one or more gamma ray detectors of the positron emission tomography scanner;

classifying each annihilation event based on respective extracted energy data and respective extracted timing data;

calculating a timing resolution for each annihilation event based on the classification;

determining, for each annihilation event and based on the calculated timing resolution of the annihilation event, a width of a time-of-flight kernel; and reconstructing the positron emission tomography image based on the obtained raw data from the positron emission tomography scanner and the determined width of the time-of-flight kernel associated with each annihilation event, wherein the classifying includes, for each annihilation event:

determining, from the respective extracted energy data and the respective extracted timing data, a quantity of the one or more gamma ray detectors impacted by each of the pair of gamma rays generated by the annihilation event, wherein the classifying classifies the annihilation event as a single-crystal event, a multi-crystal event, or a hybrid-crystal event based on the determined quantity of the one or more gamma ray detectors impacted by each of the pair of gamma rays generated by the annihilation event, wherein the single-crystal event is a photoelectric event, the multi-crystal event is a scattering event, and the hybrid-crystal event is a combination thereof, and wherein the calculating includes, when the classification indicates an annihilation event is a hybrid-crystal event, calculating the timing resolution by a convolution of a timing resolution associated with a single-crystal event and a timing resolution associated with a multi-crystal event.

* * * * *